United States Patent
Gai et al.

(10) Patent No.: US 11,154,729 B2
(45) Date of Patent: Oct. 26, 2021

(54) HIGH BRIGHTNESS ELECTRON BEAM BASED PRECISE RADIATION THERAPY METHOD AND SYSTEM

(71) Applicant: Shenzhen Ming-Jie Medical Science and Technologies Co. Ltd., Shenzhen (CN)

(72) Inventors: Wei Gai, Shenzhen (CN); Huijun Xu, Shenzhen (CN); Huaibi Chen, Shenzhen (CN)

(73) Assignee: Shenzhen Ming-Jie Medical Science and Technologies Co. Ltd., Shenzhen (CN)

( * ) Notice: Subject to any disclaimer, the term of this patent is extended or adjusted under 35 U.S.C. 154(b) by 427 days.

(21) Appl. No.: 15/999,149

(22) Filed: Aug. 17, 2018

(65) Prior Publication Data
US 2019/0054321 A1    Feb. 21, 2019

(51) Int. Cl.
*A61N 5/00* (2006.01)
*A61N 5/10* (2006.01)

(52) U.S. Cl.
CPC .......... *A61N 5/1077* (2013.01); *A61N 5/1031* (2013.01); *A61N 5/1071* (2013.01); *A61N 2005/1089* (2013.01)

(58) Field of Classification Search
CPC .. A61N 5/1077; A61N 5/1031; A61N 5/1071; A61N 2005/1089
See application file for complete search history.

(56) References Cited

U.S. PATENT DOCUMENTS

| | | | |
|---|---|---|---|
| 5,321,271 A * | 6/1994 | Schonberg | A61N 5/01 250/492.3 |
| 5,547,454 A * | 8/1996 | Horn | A61N 5/1001 600/1 |
| 7,312,461 B2 | 12/2007 | Lewellen et al. | |

* cited by examiner

*Primary Examiner* — Samuel G Gilbert
(74) *Attorney, Agent, or Firm* — Maine Cernota & Rardin

(57) ABSTRACT

An apparatus for applying an electron beam to a subdermal tumor generates a pulsed electron beam that is collimated to a diameter of less than 1 mm and less than 10 millimeter-milliradiant transverse emittance. A biopsy needle having an interior diameter less than 2 mm and length between 1 cm and 100 cm is inserted through the skin to the tumor, and the electron beam is electromagnetically directed through the needle, so as to reach the tumor without irradiating intervening normal tissue and with minimal irradiation of surrounding normal tissue. The electron pulsing rate can be in the S-band or Q-band, the beam energy can be between 1 Mev and 6 MeV, and/or the beam brightness can be less than 10 mm·mrad. A distal end of the biopsy needle can include an electron-permeable vacuum barrier, and the apparatus can be evacuated to less than $10^{-8}$ Torr.

18 Claims, 3 Drawing Sheets

HIGH BRIGHTNESS ELECTRON BEAM BASED PRECISE RADIATION THERAPY METHOD AND SYSTEM

RELATED APPLICATIONS

This application claims the priority of Chinese Application No. CN201710709062.3, filed Aug. 17, 2017 which is herein incorporated by reference in its entirety for all purposes.

FIELD OF THE INVENTION

The present invention relates to systems and methods for generating high brightness electron beams and precisely delivering them to organ tumors inside the human body with controllable dosage.

BACKGROUND OF THE INVENTION

Currently, human tumor radiation treatment is dominated by radiation therapy methods based on three particle species, photon (a.k.a. X-ray), proton, and heavy ion. All three families of methods utilize a sudden, heavy energy deposition onto the tumor tissue to kill the cancer cells, or to stop them from reproducing.

X-ray based radiation therapy is the most mature technology of the three. However, it is generally known as having the largest adverse effect of damaging normal tissue cells in its passage to and from the cancer cells inside the human body. Advanced multi-beam technology can reduce X-ray exposure to normal tissue cells during X-ray radiation therapy. Nevertheless, due to the strong penetration capability of the energetic X-ray photons, this limitation to applying the X-ray radiation treatment still remains.

Radiation therapy methods based on proton and heavy ion irradiation are attractive because their maximum radiation dose can be delivered to tumor within a range of a few millimeters. With proper design, the energy dose administered to normal tissue by a proton or ion beam in its passage to the tumor is only a fraction of the dose applied to the tumor itself, and the radiation energy beyond the tumor dissipates quickly. This feature is often referred as the "Bragg peak." In comparison with X-ray radiation therapy, radiation treatment based on proton and heavy ion irradiation has less collateral effect on the surrounding normal tissue, which is particularly favorable for treatment of certain cancers, for example, tumors of the prostate, brain, head and neck, central nervous system, lung, and gastrointestinal system, etc. However, proton and heavy ion radiation therapy machines are far more expensive than X-ray therapy apparatus. The capital investment is almost two orders of magnitude higher for proton and heavy ion systems, and the operation costs are also very high. Also, while typically less than for X-ray treatment, there is still some irradiation of intervening normal tissue by proton or ion beams before the beams reach the tumor when these treatments are applied.

Electron beams can be used for radiation therapy. However, an electron beam, even when energized to a few megavolts, is barely able to penetrate human skins. Therefore, electron beams can usually only be used to treat skin cancer, whereby the electron source is applied outside the human body. As an assistive measure, energized electron beam are sometimes applied near the end of a tumor-removing surgical procedure so as to kill any potential cancer cells that may be located in the tissues immediately surrounding the tumor. This extra step usually requires creating an incision of at least a few centimeters in order to allow the electron beam to be ducted into the human body to the exposure site.

What is needed, therefore, is a method of applying electron beam radiation to a tumor that is beneath the skin without creating an incision.

SUMMARY OF THE INVENTION

According to the present invention, instead of applying an electron beam to a targeted tumor inside the human body through a large surgery incision, the beam is delivered directly to the targeted tumor tissue through a special biopsy needle having an inner diameter of less than 2 mm that is punctured through the patient's body. The electron beam that is generated has a diameter that is less than one millimeter in diameter in the transverse direction, and is less than 10 millimeter-milliradiant in transverse emittance (where transverse emittance is the product of the transverse size in units of millimeters and the transverse divergence in the units of milliradiant) so that the electron beam can be conveyed through the biopsy needle. Based on the irradiation property of the electron beam, by altering the electron beam energy and current, the radiation energy can be strictly concentrated in the tumor itself. Calculations demonstrate that only a few seconds of exposure to the disclosed electron beam can deliver sufficient energy to kill cancer cells, while the surrounding tissues is not affected even when the irradiation energy is at its maximum level. As a result, any pain experienced by the patient is minimized.

Accordingly, a precise tumor radiation therapy method and system are disclosed that applies an energetic electron beam to a tumor. A pulsed electron beam is generated having an energy of between one and six MeV (Mega-electron-Volts), with minimal transverse and longitudinal size and dispersion, and is delivered to the tumor tissues through a specially engineered biopsy needle.

The disclosed therapy method and system are referred to herein as an "e-knife" method and system. The electron beam production apparatus is referred to herein as the e-knife electron source, while the specially engineered biopsy needle is referred to herein as the e-knife needle.

In embodiments, the disclosed e-knife produces the electron beam using a high frequency RF source that is approximately 10 GHz in frequency and more than 1 MW in power to drive a single electron source. In embodiments, the e-knife electron source is significantly simplified and compact in comparison with systems described in the Prior Art.

In various embodiments, the disclosed e-knife electron source is a single assembly that comprises 4 functional sections arranged in series and includes 2 auxiliary side ports. The four functional sections are:

1) the electron generating section or "gun," which emits electrons from a thermionic or field emission cathode and uses a high electric field gradient to provide an immediate acceleration of the generated electrons;
2) the electron pulsing section or "buncher," which groups the continuously emitted electrons into a train of electron pulses;
3) the electron acceleration section, which accelerates the pulsed electrons to an energy level of between 1 MeV and 6 MeV; and
4) the electron collimation section, which allows only the core of the accelerated electron beam to exit the e-knife electron source.

The two auxiliary side ports are:
1) the vacuum pumping port, which reduces the pressure in the entire e-knife electron source to less than $10^{-8}$ Torr; and
2) the RF coupling port, which feeds high power RF from the RF source to the entire e-knife electron source.

In embodiments, the e-knife needle is used to transport the electron beam through overlaying human tissues, such as skin, muscles, etc., to the targeted cancer tumor. In embodiments, the needle is a non-magnetic metal tube having an outer diameter of not more than 5 millimeters, an inner diameter of less than 2-millimeters for beam clearance, and a length of less than 100 centimeters. More than one half of the length of the needle interior remains under vacuum during use. In embodiments, the e-knife needle has a sharply bladed tip that is able to puncture through human skin and tissues. The distal end of the needle is blocked by a thin metallic film, which can be an aluminum film, which separates the portion of the needle interior that is under vacuum from the remaining portion of the needle interior, and from the exterior tissues and gases, while being transparent to the electron beam. In embodiments, the e-knife needle is also capable of measuring the electron beam current.

In embodiments, the e-knife needle is disposable after use. In various embodiments a remotely controllable compact vacuum gate valve or shutter is included between the electron source and the e-knife needle so as to maintain the vacuum within the electron source while replacing the needle. In some of these embodiments the proximal end of the e-knife needle is a flange that can be mated to the gate valve or shutter. In certain embodiments the proximal (upstream) end of the e-knife needle also includes a side opening and flange that function as a vacuum pumping port to allow the needle to be pumped to a certain vacuum level before the gate valve or shutter is open.

In embodiments of the disclosed method, a one-to-one artificial biological model is used to measure and evaluate the dose delivery profile and dose value of the e-knife prior to applying a tumor radiation treatment to a patient. This enables the treatment effect to be optimized and preserved for post analysis.

In embodiments, the disclosed e-knife system comprises:
a. A compact high quality electron beam source, referred to herein as the e-knife electron source, which provides a pulsed electron beam having between 1 MeV and 6 MeV of energy, with a pulse duration of less than 10 microseconds and an adjustable pulse repetition rate, with the transverse emittance of electron beam being less than 10 mm-mrad, and with the charge range of less than 1000 pico-Coulomb.
b. A specially engineered biopsy needle, referred to herein as the e-knife needle, which introduces and delivers the electron beam from outside of the human body to the location of the targeted tumor tissue.
c. An electron beam magnetic focusing element, which uses a solenoid magnet excited by an electrical current to focus the electron beam through the e-knife needle while avoiding impacts between the electrons and the interior wall of the needle.
d. A high power RF system, which provides Mega-Watt level RF pulses that power the e-knife electron source. The high power RF pulses can be manipulated to tune their amplitude and frequency, thus tuning the final electron beam energy as needed.
e. A vacuum pumping system to maintain the vacuum level of the entire e-knife electron source and the e-knife needle.
f. A radiation shielding system to reduce unnecessary ionizing radiation to below the levels that are allowed by safety and environmental regulations.
g. A mechanical supporting system having at least 3-degrees of freedom and an RF transportation line to ensure the maximum flexibility of accessing the targeted tumor.
h. A Computerized Treatment Planning Systems (TPS) configured to evaluate the effective dose that was delivered to the targeted tumor.

A first general aspect of the present invention is an apparatus for applying pulsed electron irradiation to abnormal subdermal tissue. The apparatus comprises an electron source configured to emit a beam of electrons, an electron collimator, configured to collimate the beam of electrons so that the beam of electrons is less than one millimeter in diameter and less than 10 millimeter-milliradiant in its transverse emittance, and a radiation delivery tube having a hollow interior that is not more than 2 mm in diameter, the radiation delivery tube being configured for insertion through a patient's skin and for delivery of the collimated beam of electrons through its hollow interior to the abnormal subdermal tissue.

In embodiments, the electron source comprises a radio frequency generator, an electron pulser configured to transfer radio frequency energy generated by the radio frequency generator to the beam of electrons, thereby converting the beam of electrons into a beam of electron pulses, and an electron accelerator, configured to accelerate the electron pulses to an energy of between 1 MeV and 6 MeV.

In any of the above embodiments, a pulsing rate of the electron pulses can be in the S-band of frequencies or the X-band of frequencies.

In any of the above embodiments, the electron gun can emit electrons using at least one of photoemission, thermal emission, and field emission.

Any of the above embodiments can further comprise an evacuation system configured to create a vacuum within the electron source, the electron collimator, and a proximal first portion of the radiation delivery tube interior. In some of these embodiments, the residual pressure of the vacuum is 10-8 torr or less. In any of these embodiments, the proximal first portion of the radiation delivery tube interior can be separated from a distal second portion of the radiation delivery tube interior by a barrier that is impermeable to air, but permeable to the beam of electrons. In some of these embodiments, the barrier is a film or foil. And in some of these embodiments, the barrier comprises at least one of aluminum, titanium, beryllium, and polyamide.

In any of the above embodiments, the radiation delivery tube can be made from a non-magnetic material, and the collimator comprises an electromagnetic beam focusing element that is able to direct the beam of electrons through the interior of the radiation delivery tube with minimal impact to its interior walls.

In any of the above embodiments, the beam of electrons can have a brightness of less than 10 mm·mrad.

In any of the above embodiments, the beam of electrons can have an energy of between 1 MeV and 100 MeV.

In any of the above embodiments, the radiation delivery tube can be between 1 cm and 100 cm in length.

In any of the above embodiments, the radiation delivery tube can have an outer diameter that is no more than 5 mm.

A second general aspect of the present invention is a method of applying radiation treatment to abnormal, subdermal tissue. The method comprises inserting a distal end of a hollow radiation delivery tube through the skin of a patient so that the distal end abuts or enters into the abnormal tissue, the radiation delivery tube having an interior diameter of not more than 2 mm, causing an electron source to generate a beam of electrons, causing an electron beam collimator to collimate the beam of electrons so that the beam of electrons is less than one millimeter in diameter and less than 10 millimeter-milliradiant in its transverse emittance, and directing the collimated beam of electrons into the hollow interior of the radiation delivery tube, so that the collimated beam of electrons is delivered directly to the abnormal tissue while being required to traverse substantially no intervening normal tissue.

In embodiments, generating the beam of electrons comprises generating a beam of electron pulses having a pulse frequency in the S-band or X-band, having a brightness of less than 10 mm·mrad, and having an energy between 1 MeV and 6 MeV.

Any of the above embodiments can further include evacuating to a residual pressure of less than 10-8 Torr the electron source, the collimator, and a proximal first portion of the radiation delivery tube interior, the first portion being separated from a distal, second portion of the radiation delivery tube interior by a barrier that is impenetrable to air, but penetrable by the beam of electrons.

And in any of the above embodiments, directing the beam of electrons into the hollow interior of the radiation delivery tube can include controlling a flow of electric current through an electromagnet beam focusing element.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

The advantages and features of the present invention will become better understood with reference to the following more detailed description and claims taken in conjunction with the accompanying drawings.

Figure 1:
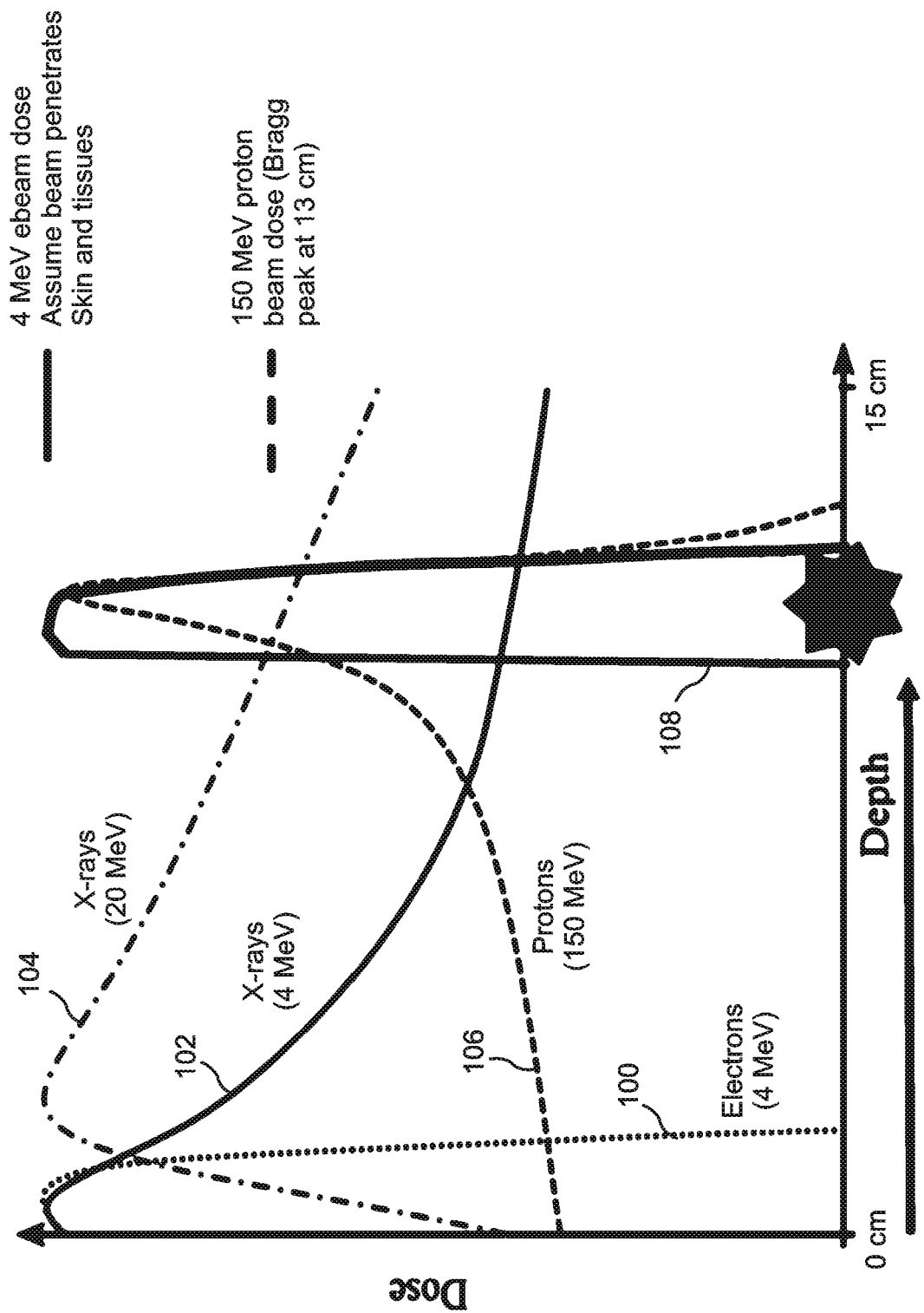
FIG. 1 is a graph that illustrates irradiation dosage distribution profiles of three different particle species (X-ray photon, electron, and proton)

With the reference to FIG. 1, the irradiation properties of three typical particle species (X-ray photon at 4 MeV and 20 MeV, electron, and proton) are plotted in one graph for comparison. In the plot, the vertical axis is the normalized radiation dose for different energetic radiation particles, and the horizontal axis represents the irradiation depth directed into the human body when the irradiation source is placed outside the human body. It can be seen from the dotted line 100 in the graph that the 4-MeV electron beam, if placed outside the skin, has a very sharp falling edge at one to two centimeters into the human body, which is typically insufficient to reach most human organs. The black solid line 102 represents the irradiation pattern of the X-ray photons generated by the Bremsstrahlung radiation of a 4 MeV electron beam hitting on the thin film target commonly used in the medical X-ray radiation therapy machine. In contrast to the electron beam, the X-ray dose shows a slow decay over a 15 cm range, which is usually sufficient to extend across an entire human body from the chest to back. When the X-ray energy is increased, as shown in the dot-dash line 104 which represents the X-rays generated by a 20 MeV electron Bremsstrahlung radiation, the radiation dose peaks at a few centimeters into the body and then begins to decay, but nevertheless remains at a high level across the entire body. The dashed line 106 represents the irradiation pattern of a 150 MeV proton beam where a clear narrow high dose peak occurs at about 13 centimeters into the body then rapidly decays. This irradiation feature is very attractive to certain types of cancers considering the reduced damage to the normal cells in the irradiation passage in comparison of the X-ray radiation.

The heavier solid line 108 with a 7-pointed star below it represents the physical foundation of the present invention. Unlike the other curves in FIG. 1 (100-104) which are based on actual measurements, the heavy solid line 108 was plotted by shifting the dotted line 100 (representing a radiation dose of 4 MeV electrons outside the skin) to the 13-centimeter location inside the human body. It indicates that, if the 4-MeV electrons can be applied directly to the targeted human tissues needing to pass through other, irrelevant tissues, the radiation dose will be localized within a one to two centimeters region 108. This radiation "gating" phenomenon has an unprecedented advantage over all other radiation therapy methods, because it can provide a high efficiency radiation treatment applied to the tumor itself with negligible damage to the surrounding normal tissues. The size of the irradiated region can be adjusted as needed by adjusting the beam energy and current.

Based on the physics of radiation gating as described above, the present apparatus and method generates a high brightness electron beam of more than 1 MeV (where the brightness is defined herein as the degree of confinement of electrons in terms of their momentum and positions in all directions within a region that is as small as possible) and delivers the generated electrons directly to the target via a biopsy needle having an inner diameter that is typically less than 2 mm. The radiation dose applied by an embodiment of the invention was mapped using a water target, and the results confirm the feasibility of the disclosed apparatus and method. While applying a radiation treatment to a tumor, the needle can either be positioned outside of the boundary of the tumor and/or penetrated into the tumor as the energetic electrons are released. Because there is no energy loss before the electrons reach their target, the disclosed method has highest possible efficiency in terms of radiation dose delivery. Therefore, treatment times can be significantly reduced in comparison with other radiation methods. Because of the predictably significant increase of treatment effectiveness compared to other methods, the apparatus and method of the present invention are referred to herein as an "e-knife."

The electron beam generated by the e-knife system as described above also exhibits a superior directivity, analogous to the collimation of a laser beam, so that its transverse envelope out of the accelerator is far less than the aperture of the biopsy needle. The figure of merit characterizing an electron beam in the transverse plane is the transverse emittance. In embodiments, the transverse emittance of the disclosed e-knife system is less than 1 milimeter-miliradiant at an intensity as characterized in terms of electrons per pulse of between 100 and 500 pico-coulombs). The energy of the e-knife system is in the range of 1 MeV to 100 MeV.

Figure 2:
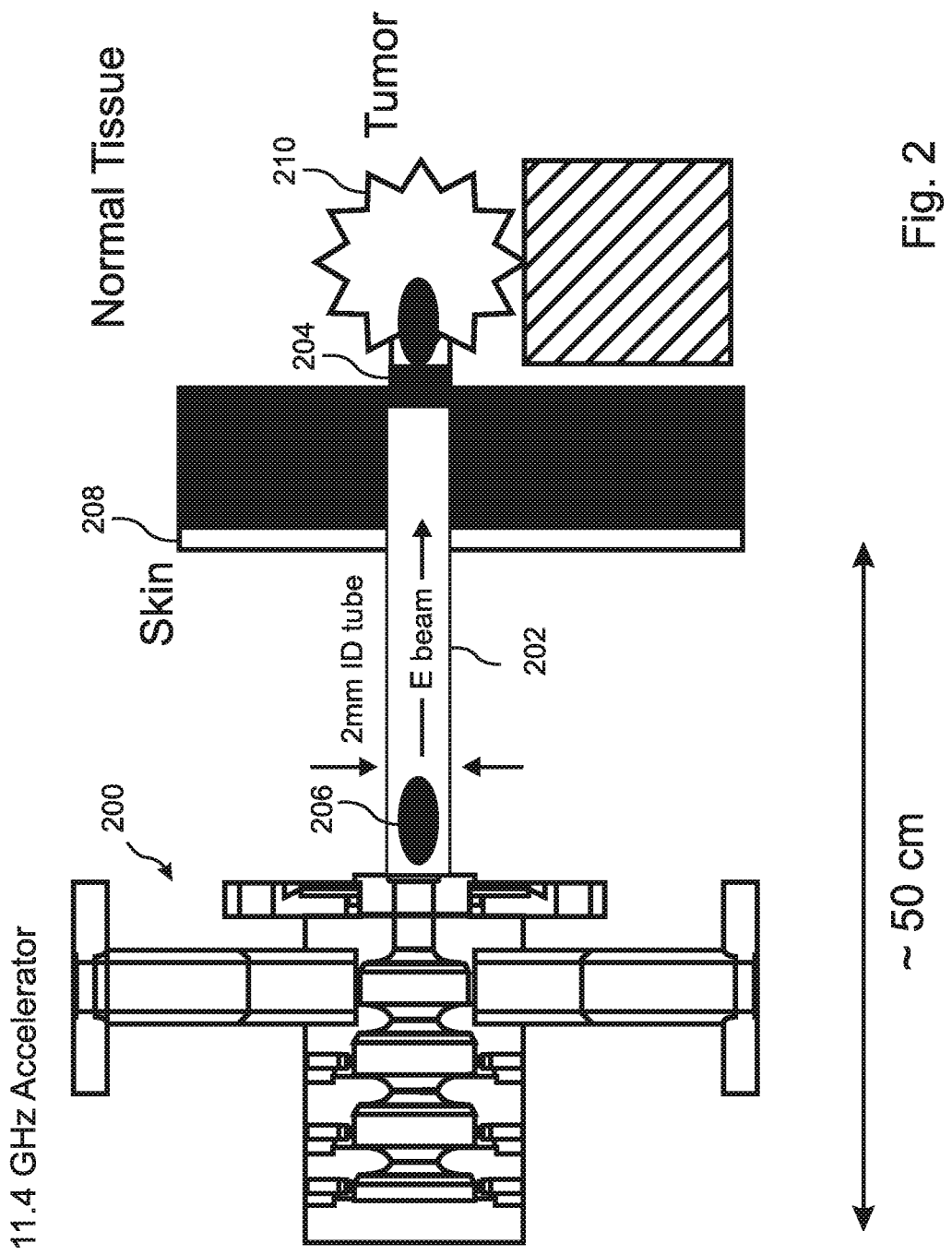
FIG. 2 is a block diagram that illustrates the working principle of a simplified e-knife system according to the present invention.

With the reference of FIG. 2, in embodiments, the electrons that are emitted from the cathode are accelerated to a desired energy level (e.g. 4 MeV) in an a RF accelerator 200. The inner volume of accelerator 200 is under vacuum. The electrons 206 are focused to directly propagate through the biopsy needle 202, which in embodiments has a length in the range of 10 cm to 30 cm, depending upon the location of the targeted tumor. The inner diameter of the biopsy needle 202 in embodiments is less than or equal to 2 mm. Most of the interior volume of the needle 202 is evacuated through a connection (not shown) with the accelerator 200. A thin foil or film 204, such as a foil of aluminum or a film of polyamide film (such as Kapton™ film made by DuPont), is located near the distal end of the needle 202, so as to separate the evacuated portion of the needle 202 from the un-evacuated portion and the outside environment, while allowing the electrons 206 go through the needle 202 with a minimal loss of energy. According to the disclosed method, the biopsy needle 202 is punctured through the patient's skin 208 until it reaches the tumor 210. The electrons 206 emerging from the distal end of the needle 202 will rapidly deposit all of their energy onto the tumor 210 within a distance of between 2 cm and 3 cm from the distal end of the tube 202.

With the reference of FIG. 2, the e-knife system has the mostly simplified the configuration which is able to deliver the energetic electrons 202 directly to the targeted tumor tissues without the need to generate gamma rays. The precise localization of the electrons eliminates most or all damage to healthy tissues. In the entire treatment process of the disclosed method, the patient only needs to undergo a small incision from the biopsy needle, which significantly reduces the patient's pain and other associated side-effects as compared to more invasive methods, and thus improves the post-treatment life quality of the cancer patient. Another benefit of the disclosed method and system is that the simple configuration of e-knife system significantly reduces the requirements of radiation shielding, thereby requiring less space within the treatment room. The simple configuration also reduces the complexity of the gantry design.

Producing the High Brightness Electron Beam

During the past two decades, driven in part by the requirements of free electron laser light sources and electron-positron linear colliders, rapid progress has been made by the scientific community worldwide in the development of high brightness electron beam apparatus. The present invention further defines the high brightness beam, and produces a beam having less than 10 mm-mrad of normalized transverse emittance and between 1 MeV and 100 MeV of kinetic energy. The resulting high brightness electron beam, which is conveyed almost without loss via an evacuated needle that is up to 10 cm long (or longer), and 2 mm or less in its inner diameter, thus reaching the patient's targeted tumor tissue with almost no attenuation or inadvertent irradiation of surrounding normal tissue. Production of the high brightness beam of the present invention requires two steps, which are the electron beam emission and the electron beam acceleration. Each of these steps is critical to the final result.

High Brightness Beam Emission

The high brightness electron gun, which can mitigate space charge effects by applying a high accelerating gradient, is a common device that is used to generate high brightness electron beams. Electrons emitted from the cathode surface of the electron gun are generated using any of three difference emission mechanisms: photoemission, thermal emission, and field emission. With current technology development, the high brightness electron beam required in this invention can be produced with any one of three cathodes. The optimal approach for each application of the present invention will be selected through considerations of the comprehensive balance among the electron emittance, the cathode lifetime, and the fabrication cost.

High Brightness Beam Acceleration

Figure 3A:
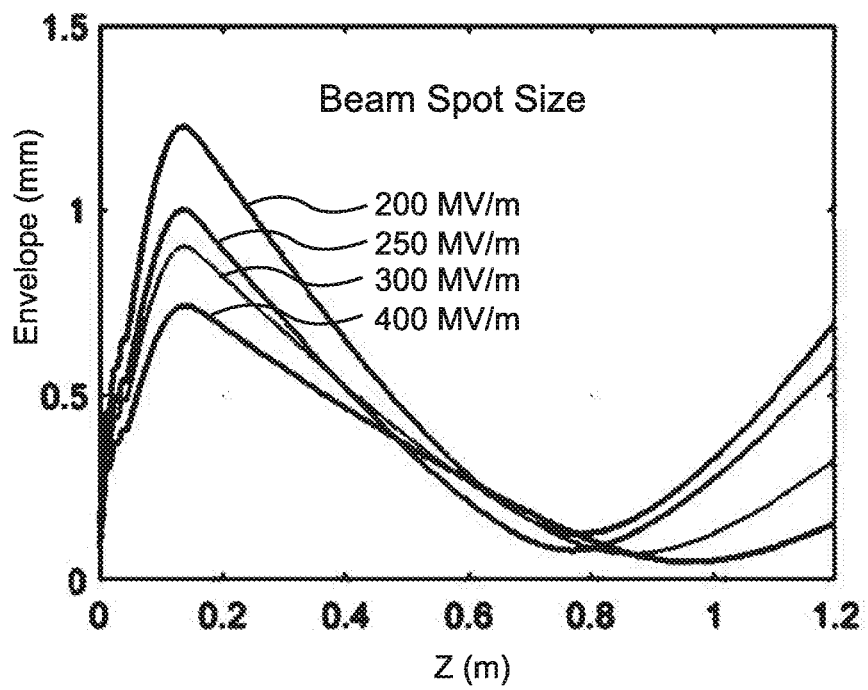
FIG. 3A is a graph of a simulated electron beam size envelope over a distance of between zero and 1.2 meters that can be produced and delivered through the e-knife system of FIG. 2.
Figure 3B:
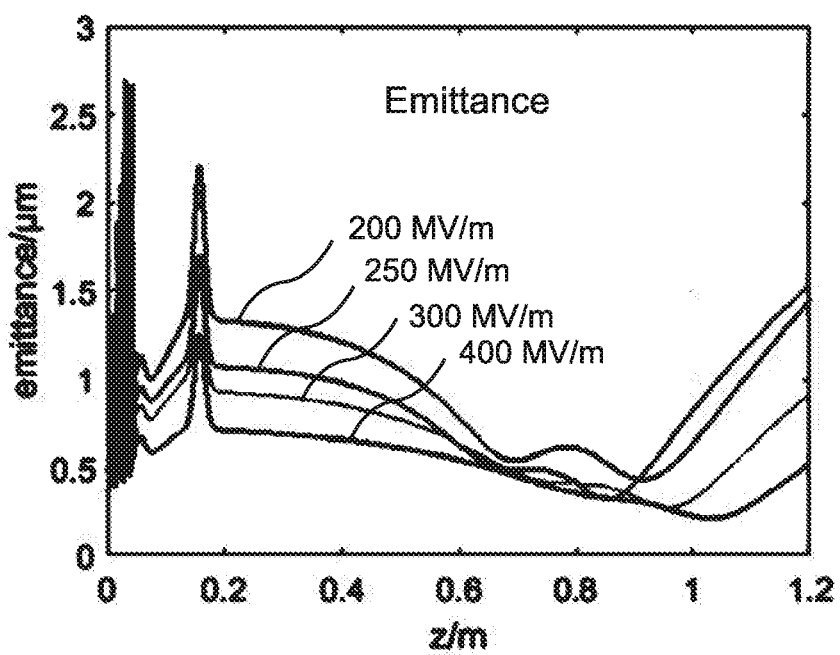
FIG. 3B is a graph of simulated electron beam divergence over a distance between zero and 1.2 meters that can be produced and delivered through the e-knife system of FIG. 2.

After being emitted from the cathode, the electrons continuously gain energy in an electron accelerator, which transfers a fraction of received RF wave energy to the kinetic energy of electrons. Electron accelerators that are sufficient for application to the present invention are well known in the art, such that enablement of the present invention does not require a detailed description of such electron accelerators. FIGS. 3A and 3B illustrate the resulting properties of a beam produced by an X-band (11.424 GHz) high gradient accelerator injector as an illustrative example, showing that a well-adjusted beam with 200 pico-Coulomb charge from a photocathode RF gun can travel in a small, evacuated tube for long distances (10-40 cm). FIG. 3A illustrates a simulated the electron beam envelope over a distance of more than 1-meter from the cathode. The electron beam is emitted at Z=0, and then accelerated over the next 0.1 meter with accelerating fields ranging from 200 MV/m to 400 MV/m. In similar embodiments, lower fields can produce beams having similar characteristics. The beam transverse emittance is illustrated in FIG. 3B.

Electron Beam Transmission

Due to the small transverse dimension of the compact electron accelerator in embodiments of the present invention, external magnets can be easily applied in embodiments to focus the low emittance beam during its acceleration. This can enable the electron beam to propagate through an e-knife needle having a length of 50 cm or more without significant beam loss until it reaches the target tissue and delivers a dose at a rate that can be as high as 10-100 Gy/min. The e-knife biopsy needle can be made of a rigid, non-magnetic material. Its diameter can be less than 5 millimeters, and its length can be between 1 and 100 cm. The biopsy needle can be disposable after one usage, and embodiments can be easily detached from the accelerator.

Electron Beam Energy Deposition

The dose delivery capability of an e-knife device according to the present invention can be estimated as follows. If the e-knife accelerator, for example, can produce 4 MeV, 200 pC (pico-Coulomb) electrons at a repetition rate of 100 Hz, then the beam will deliver 80 Joules of energy per second. Given that the beam deposits all of its energy within a 1 cubic centimeter volume, this is equivalent to 80 Gy/second of dosage, which is a rate that will certainly kill almost any cancerous tissues within one second. Different scenarios can be scaled from this example, such as higher energy beams for larger tumors, and modified beam deliver system for tumors having different shapes.

Radiation Protection of the e-Knife System

The compactness of e-knife system in the present invention, which is the result of using a high gradient rf electron accelerator, an integrated electron source, and a detachable biopsy needle, significantly simplifies the measures that are needed to prevent exposure of the patient and of operating personnel to unnecessary radiation during the treatment process. According to a Monte Carlo simulation and experimental verification, local shielding around the e-knife system that is made of a 3 mm thick sheet of lead is sufficient to protect an e-knife operator. As the result, the overall lead weight can be limited to 20 kilograms. Therefore, the expense of a treatment room with massive shielding, as is usually required for other radiation therapy systems, can be avoided.

In summary, the e-knife system as described herein differs from known radiation therapy methods and systems of the prior art at least due to the following:

In the disclosed e-knife system, the electron beam is accelerated and conveyed through a biopsy needle directly to the targeted tumor tissue, which can be located almost anywhere in the human body. The electron energy is directly deposited into the tumor tissue, so that the cancerous tissue ceases its reproduction and typically shrinks and diminishes after a single treatment, and even more after multiple treatments. The special e-knife biopsy needle is very thin, and in embodiments includes a sharp tip, so that it can puncture through human skin and tissues to reach the radiation target without requiring an incision or other surgical operation. As a result, the cutting or other damage to the intervening and surrounding normal tissues is very limited. Other benefits include the high one-time dosage, low energy loss, low damage to normal tissue, no gamma ray generation, and less accommodation requirements due to compact structures, etc.

The following Table summarizes differences between the e-knife and other existing radiation therapy methods. Note, numbers of * represents the level scale.

TABLE 1

Summary of differences between the e-knife and other existing radiation therapy methods.

| | Therapy principle | Penetration through normal tissue | Damage | Effect on normal tissue | Radio-active |
|---|---|---|---|---|---|
| e-knife | ionizing radiation | N | * | ***** | ***** |
| surgery | surgical removal | Y | ***** | *** | N |
| argon-helium knife | cryotherapy | Y | **** | *** | N |
| intraoperative X-ray | ionizing radiation | Y | ***** | *** | *** |
| intraoperative electron therapy | ionizing radiation | Y | ***** | **** | **** |
| external X-radiation | ionizing radiation | Y | *** | ** | ** |
| external electron therapy | ionizing radiation | Y | *** | *** | ** |
| proton therapy | ionizing radiation | Y | ** | *** | *** |
| heavy ion radiotherapy | ionizing radiation | Y | ** | *** | **** |
| high-intensity focused ultrasound | thermal effect | Y | *** | ** | N |
| Microwave therapy | thermal effect | Y | **** | ** | N |
| laser knife | thermal effect | Y | *** | ** | N |

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

Although the present application is shown in a limited number of forms, the scope of the invention is not limited to just these forms, but is amenable to various changes and modifications without departing from the spirit thereof. The disclosure presented herein does not explicitly disclose all possible combinations of features that fall within the scope of the invention. The features disclosed herein for the various embodiments can generally be interchanged and combined into any combinations that are not self-contradictory without departing from the scope of the invention. In particular, the limitations presented in dependent claims below can be combined with their corresponding independent claims in any number and in any order without departing from the scope of this disclosure, unless the dependent claims are logically incompatible with each other.

We claim:

1. An apparatus for applying pulsed electron irradiation to abnormal subdermal tissue, the apparatus comprising:
   an electron source configured to emit a beam of electrons;
   an electron collimator, configured to collimate the beam of electrons so that the beam of electrons is less than one millimeter in diameter and less than 10 millimeter-milliradiant in its transverse emittance; and
   a radiation delivery tube having a hollow interior that is not more than 2 mm in diameter, the radiation delivery tube being configured for insertion through a patient's skin and for delivery of the collimated beam of electrons through its hollow interior to the abnormal subdermal tissue.

2. The apparatus of claim 1, wherein the electron source comprises:
   a radio frequency generator;
   an electron pulser configured to transfer radio frequency energy generated by the radio frequency generator to the beam of electrons, thereby converting the beam of electrons into a beam of electron pulses; and
   an electron accelerator, configured to accelerate the electron pulses to an energy of between 1 MeV and 6 MeV.

3. The apparatus of claim 2, wherein a pulsing rate of the electron pulses is between 2 GHz and 4 GHz, or between 8 GHz and 12 GHz.

4. The apparatus of claim 1, wherein the electron source emits electrons using at least one of photoemission, thermal emission, and field emission.

5. The apparatus of claim 1, further comprising an evacuation system configured to create a vacuum within the electron source, the electron collimator, and a proximal first portion of the radiation delivery tube interior.

6. The apparatus of claim 5, wherein the vacuum has a residual pressure of $10^{-8}$ torr or less.

7. The apparatus of claim 5, wherein the proximal first portion of the radiation delivery tube interior is separated from a distal second portion of the radiation delivery tube interior by a barrier that is impermeable to air, but permeable to the beam of electrons.

8. The apparatus of claim 7, wherein the barrier is a film or foil.

9. The apparatus of claim 8, wherein the barrier comprises at least one of aluminum, titanium, beryllium, and polyamide.

10. The apparatus of claim 1, wherein the radiation delivery tube is made from a non-magnetic material, and the collimator comprises an electromagnetic beam focusing element that is able to direct the beam of electrons through the interior of the radiation delivery tube with minimal impact to its interior wall.

11. The apparatus of claim 1, wherein the beam of electrons has a brightness of less than 10 mm·mrad.

12. The apparatus of claim 1, wherein the beam of electrons has an energy of between 1 MeV and 100 MeV.

13. The apparatus of claim 1, wherein the radiation delivery tube is between 1 cm and 100 cm in length.

14. The apparatus of claim 1, wherein the radiation delivery tube has an outer diameter that is no more than 5 mm.

15. A method of applying radiation treatment to abnormal, subdermal tissue, the method comprising:

inserting a distal end of a hollow radiation delivery tube through the skin of a patient so that the distal end abuts or enters into the abnormal tissue, the radiation delivery tube having an interior diameter of not more than 2 mm;

causing an electron source to generate a beam of electrons;

causing an electron beam collimator to collimate the beam of electrons so that the beam of electrons is less than one millimeter in diameter and less than 10 millimeter-milliradiant in its transverse emittance; and directing the collimated beam of electrons into the hollow interior of the radiation delivery tube, so that the collimated beam of electrons is delivered directly to the abnormal tissue while being required to traverse no intervening normal tissue.

16. The method of claim 15, wherein generating the beam of electrons comprises generating a beam of electron pulses having a pulse frequency between 2 GHz and 4 GHz, or between 8 GHz and 12 GHz, having a brightness of less than 10 mm·mrad, and having an energy between 1 MeV and 6 MeV.

17. The method of claim 15, further comprising evacuating to a residual pressure of less than $10^{-8}$ Torr the electron source, the collimator, and a proximal first portion of the radiation delivery tube interior, the first portion being separated from a distal, second portion of the radiation delivery tube interior by a barrier that is impenetrable to air, but penetrable by the beam of electrons.

18. The method of claim 15, wherein directing the beam of electrons into the hollow interior of the radiation delivery tube comprises controlling a flow of electric current through an electromagnet beam focusing element.

* * * * *

UNITED STATES PATENT AND TRADEMARK OFFICE
CERTIFICATE OF CORRECTION

PATENT NO. : 11,154,729 B2
APPLICATION NO. : 15/999149
DATED : October 26, 2021
INVENTOR(S) : Wei Gai, Huijun Xu and Huaibi Chen Page 1 of 1

It is certified that error appears in the above-identified patent and that said Letters Patent is hereby corrected as shown below:

On the Title Page

Item (30), Foreign Application Priority Data should read CN 201710709062.3 filed August 17, 2017

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*